(12) United States Patent
Schiefer et al.

(10) Patent No.: US 9,045,402 B2
(45) Date of Patent: Jun. 2, 2015

(54) PROCESS FOR PREPARING CHIRAL QUINONE

(71) Applicant: DSM IP ASSETS B.V., Heerlen (NL)

(72) Inventors: Gerhard Schiefer, Basel (CH); Thomas Netscher, Basel (CH); Alexander Lucia Leonardus Duchateau, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 14/241,288

(22) PCT Filed: Sep. 21, 2012

(86) PCT No.: PCT/EP2012/068641
§ 371 (c)(1),
(2) Date: Feb. 26, 2014

(87) PCT Pub. No.: WO2013/041676
PCT Pub. Date: Mar. 28, 2013

(65) Prior Publication Data
US 2014/0206905 A1   Jul. 24, 2014

(30) Foreign Application Priority Data
Sep. 23, 2011   (EP) .................................. 11182428

(51) Int. Cl.
| C07C 46/10 | (2006.01) |
| C07C 37/00 | (2006.01) |
| C07C 37/14 | (2006.01) |
| C07C 45/71 | (2006.01) |
| C07C 46/00 | (2006.01) |

(52) U.S. Cl.
CPC .................. *C07C 46/10* (2013.01); *C07C 37/14* (2013.01); *C07C 45/71* (2013.01); *C07C 46/00* (2013.01); *C07B 2200/07* (2013.01); *C07C 37/002* (2013.01)

(58) Field of Classification Search
USPC .................................................. 568/315, 766
See application file for complete search history.

(56) References Cited

U.S. PATENT DOCUMENTS

| 6,096,907 A | 8/2000 | Baldenius et al. |
| 2011/0172312 A1* | 7/2011 | Miller et al. ................. 514/690 |

OTHER PUBLICATIONS

International Search Report for PCT/EP2012/068641 mailed Oct. 11, 2012.
W. Shrader et al., "Alpha.-Tocotrienol Quinone Modules Oxidative Stress Response and the Biochemistry of Aging", Bioorganic & Medicinal Chemistry Letters, 21(12), XP002663593, pp. 3693-3698, Apr. 24, 2011.
H. Kabbe et al., "A New Synthesis of 3,4-Dehydro-alpha.-tocotrienol and Vitamin E", (12), XP-002663594, pp. 888-889, Dec. 1978.

* cited by examiner

*Primary Examiner* — Sikarl Witherspoon
(74) *Attorney, Agent, or Firm* — Nixon & Vanderhye P.C.

(57) ABSTRACT

The present invention relates to a process of preparing tocotrienol quinones. It has been found that this process allows the formation of the R-isomer in a high yield in a very efficient and economically interesting way. Said process is particularly useful when implemented in an industrial process. Furthermore, it has been found that this process allows using isomer mixtures as they result from traditional industrial synthesis.

18 Claims, 5 Drawing Sheets

Fig. 9 Chromatograms of separation of (RS)-6-hydroxy-2,5,7,8-tetramethyl-2-((3E,7E)-4,8,12-trimethyltrideca-3,7,11-trienyl) chroman-4-one

PROCESS FOR PREPARING CHIRAL QUINONE

This application is the U.S. national phase of International Application No. PCT/EP2012/068641 filed 21 Sep. 2012 which designated the U.S. and claims priority to EP 11182428.0 filed 23 Sep. 2011, the entire contents of each of which are hereby incorporated by reference.

TECHNICAL FIELD

The present invention relates to the field of tocotrienol quinones and tocotrienols as well as derivates thereof.

BACKGROUND OF THE INVENTION

It is known that α-tocotrienol quinones are pharmaceutically active.

US 2011/0172312 A1 discloses that tocotrienol quinones are used in treating Leight Syndrome. WO 2010/126909 A1 and US 2006/0281809 A1 disclose that tocotrienol quinones can be used for treating ophthalmic diseases and mitochondrial diseases. U.S. Pat. No. 5,318,993 discloses the activity of tocotrienol quinones as cholesterol suppression. W. D. Shrader et al., Bioorganic & Medical Chemistry Letters 21 (2011), 3693-3698 disclose that the R-isomer of α-tocotrienol quinone is a metabolite of α-tocotrienol and is a potent cellular protectant against oxidative stress and ageing. The R-isomer of α-tocotrienol used for this study has been extracted from *Elaeis guineensis*. All these documents either use tocotrienol from natural sources or do not disclose the source of tocotrienol respectively tocotrienol quinones or disclose very specific complex synthesis thereof. These methods are very expensive and limited in producing industrial amounts of the desired products.

It is well known that from vitamin E the tocopherols and tocotrienols having the R-configuration have a significantly higher bioactivity (biopotency) than the corresponding S-isomer. This is also the case for the corresponding R-isomers of tocotrienol quinones.

Synthetic pathways to produce the R-isomer of tocotrienol quinones in a stereospecific way are very expensive and therefore only of limited interest. The synthesis of α-tocotrienol is known from Kabbe and Heitzer, *Synthesis* 1978, 888-889, however, no indication of chirality whatsoever is indicated.

The synthesis of tocotrienol from the corresponding 4-oxo-chromanol-derivative is known from U.S. Pat. No. 6,096,907, however, no indication of chirality is indicated.

*J. Org. Chem.* 1981, 46, 2445-2450 and CH 356754 disclose the chemical transformation of α-tocopherol to α-tocopheryl quinone and to α-tocopherylhydro-quinone, however, neither tocotrienols nor tocotrienol quinones are mentioned.

Separation of chiral compounds by chromatography is principally known. However, it is also known that the quantitative separation is very often very difficult to achieve.

Due to the importance of these substances, there exists a high interest in a process which would produce R-tocotrienol quinones in a large scale in an easy and economic way.

SUMMARY OF THE INVENTION

Therefore, the problem to be solved by the present invention is to offer an efficient and industrial process which allows preparing the R-isomer of tocotrienol quinone in a very high enantiomeric purity.

Surprisingly, it has been found that the process according to claim 1 is able to solve this problem.

Particularly, it has been found that the specific combination of process steps and the proposed reaction pathways yield the desired product. By this process it is achieved to get the tocotrienol quinones in the desired R-configuration in a high yield.

It has been shown that the chiral separation is particularly efficient when specific chiral phases and/or chiral chromatographic separation techniques are used for the separation of the tocotrienols, respectively their precursors.

In a preferred embodiment of the invention it can be achieved that the (undesired) S-isomers which are separated by the chromatographic step can be transformed into the desired R-isomers. This leads to the big advantage that the undesired S-isomer, which is typically about 50% of the isomer mixture, is not needed to be destroyed or disposed but can be transferred to a valuable product. This is economically and ecologically particularly advantageous and, therefore, represents a remarkable and important step forward in the development in this field of technology. In a preferred embodiment in which the process is a continuous process and comprises isomerization of the S-isomer this process even allows essentially 100% of the product to yield the desired R-isomer without the need of an expensive stereospecific synthesis.

The present process is particularly important as the R-isomers of tocotrienol quinones are biologically and pharmaceutically important compounds which can be used in the food, feed and pharmaceutical industry.

Further aspects of the invention are subject of further independent claims. Particularly preferred embodiments are subject of dependent claims.

BRIEF DESCRIPTION OF THE DRAWING FIGURES

FIG. 1 *a*) shows schematically the different possibilities in the variant Var. I;

FIG. 1 *b*) shows schematically the different possibilities in the variant Var. II;

DETAILED DESCRIPTION OF THE INVENTION

In a first aspect the present invention relates to a process of preparing tocotrienol quinone of formula (A).

(A)

This process comprises the steps
a) providing an isomeric mixture of compounds of formula (I-A)

(I-A)

b) chemically transforming compound of formula (I-A) to compound of formula (I-B)

(I-B)

c) chemically transforming compound of formula (I-B) or of formula (I-A) to compound of formula (I-C)

(I-C)

d) chromatographic separation of the mixture of isomers of formula (I-A) or (I-B) or (I-C) by means of a chiral phase into the R-isomer (I) and residual (I');
e) collecting the R-isomer (I) being obtained by step d);
f) chemically transforming the R-isomer of compound of formula (I-C), represented by formula (II), to tocotrienol quinone of formula (A)

(II)

wherein $R^1$, $R^3$ and $R^4$ are independently from each other hydrogen or methyl groups;

$R^2$ represents hydrogen or a phenol protection group;
$R^5$ represents a residue of formula (II-B)

(II-B)

and wherein * represents the chiral centre of the chiral isomer of formula (I-A) or (I-B) or (I-C);

The step b) is optional and the steps d) and e) take place either after step a) or after step b) or after step c).

The term "independently from each other" in this document means, in the context of substituents, moieties, or groups, that identically designated substituents, moieties, or groups can occur simultaneously with a different meaning in the same molecule.

In the present document any dotted line represents the bond by which a substituent is bound to the rest of a molecule.

A "$C_{x-y}$-alkyl", resp. "$C_{x-y}$-acyl" group, is an alkyl resp. an acyl group comprising x to y carbon atoms, i.e. for example an $C_{1-3}$-alkylgroup, is an alkyl group comprising 1 to 3 carbon atoms, and can be linear or branched.

The term "alkyl group" is in the present document to be understood as to be limited not only to strictly, i.e. completely, saturated substituents consisting of C and H, but also to comprise such substituents consisting of C and H having at least one carbon-carbon double bond. Therefore, for example, —$CH_2$—$CH_2$—$CH_2$—$CH_2$—$CH(CH_3)$—$CH_3$ as well as —$CH_2$—CH=CH—$CH_2$—$CH(CH_3)$—$CH_3$ are considered both to be $C_7$-alkyl groups.

The term "essentially" is used in the present document as to indicate amounts of more than 95%, particularly more than 98%, preferably more than 99%.

The "$pK_a$" is commonly known as negative decadic logarithm of the acid dissociation constant ($pK_a=-\log_{10} K_a$). When the organic acid has several protons the $pK_a$ relates to the dissociation of the first proton ($K_{a1}$). The $pK_a$ values indicated are at room temperature. The person skilled in the art knows that the acidities of certain acids are measured in adequate solvents and may vary upon individual measurements or due to the fact the determination of the $pK_a$ has been measured in different solvents and hence different $pK_a$ values can be found for a specific acid. Hence, in a critical case, where for an acid different $pK_a$ values can be found in literature of which at least one is in the $pK_a$ range indicated by the present document—whereas other values are found being outside of said range—it is defined that such an acid is considered to be in the range of $pK_a$ values.

Preferred are the following combinations of $R^1$, $R^3$ and $R^4$:

or or or

Most preferably the chiral isomers of formula (I-A) or (I-B) or (I-C) are the isomers (I-C) selected from the group consisting of α-Tocotrienol ($R^1=R^3=R^4=CH_3$, $R^5=$(II-B), $R^2=$H),
β-Tocotrienol ($R^1=R^4=CH_3$, $R^3=$H, $R^5=$(II-B), $R^2=$H),
γ-Tocotrienol ($R^1=$H, $R^3=R^4=CH_3$, $R^5=$(II-B), $R^2=$H),
δ-Tocotrienol ($R^1=R^3=$H, $R^4=CH_3$, $R^5=$(II-B), $R^2=$H), and the esters, particularly the acetates ($R^2=COCH_3$), thereof, respectively the corresponding precursors of formula (I-A) or (I-B) thereof.

$R^2$ represents either H or a phenol protection group. A protection group is a group which protects the phenolic group ($R^2=$H) and can be deprotected easily, i.e. by state-of-the-art methods, to the phenolic group again.

These two embodiments are structurally strongly related as they can be converted easily to each other by protection resp. deprotection reaction.

The phenol protection group forms with the rest of the molecule a chemical functionality which is particularly selected from the group consisting of ester, ether or acetal. The protection group can be easily removed by standard methods known to the person skilled in the art.

In case where the phenol protection group forms with the rest of the molecule an ether, the substituent $R^2$ is particularly an linear or branched $C_{1-10}$-alkyl or cycloalkyl or aralkyl group. Preferably the substituent $R^2$ is a benzyl group or a substituted benzyl group, particularly preferred a benzyl group.

In case where the phenol protection group forms with the rest of the molecule an ester, the substituent $R^2$ is an acyl group. The acyl group is particularly a $C_{1-7}$-acyl, preferably acetyl, propionyl or benzoyl group, or a substituted benzoyl group.

It is preferred that the protection group is a benzoyl group or a $C_{1-4}$-acyl group, particularly acetyl group. The molecules in which $R^2$ represents an acyl group, particularly an acetyl group, can be easily prepared from the corresponding phenolic ($R^2=$H) compound by esterification, respectively the phenolic compound can be obtained from the corresponding ester by ester hydrolysis. Those reactions and their reaction conditions are well known to the person skilled in the art.

In case where the phenol protection group forms with the rest of the molecule an acetal, the substituent $R^2$ is preferably with n=0 or 1.

Hence, the acetals formed so are preferably methoxymethyl ether (MOM-ether), β-methoxyethoxymethyl ether (MEM-ether) or tetrahydropyranyl ether (THP-ether). The protection group can be easily removed by acid.

In case that $R^2$ is a phenol protection group it is preferred that in a step i) the protection group is removed and that said step i) takes place before or after or during anyone of the steps b) to g) or before or during step f) he protection group.

In a preferred embodiment $R^2$ is H.

The process of preparing tocotrienol quinone of formula (A) comprises as a first step a) of a) providing an isomeric mixture of compounds of formula (I-A)

A preferred way of synthesizing compounds of formula (I-A) is from the corresponding 2-acetyl-methylhydroquinone, 2-acetyl-dimethylhydroquinone resp. 2-acetyl-trimethylhydroquinone of formula (III-A) with $R^2=$H, or the corresponding compound of formula (III-A) with $R^2$ being a phenol protecting group, and farnesylacetone of formula (IV-A) in the presence of a base, particular in the presence of pyrrolidine, as disclosed in detail by Kabbe and Heitzer, *Synthesis* 1978, 888-889 the whole disclosure of which is incorporated herein by reference. The phenol protecting group can be introduced by reacting compound of formula (I-A) having $R^2$ being H with a corresponding protecting agent. Kabbe and Heitzer disclose the introduction of an acetyl group by its reaction with acetic anhydride in the presence of pyridine and toluene.

This synthesis is not stereospecific and hence a mixture of isomers of formula (I-A) of R- and S-configuration at the chiral centre marked by * is formed. Typically racemic mixtures of about 50% S- and 50% R-isomers are formed.

Chemical Transformation Steps

The process of preparing tocotrienol quinone of formula (A) comprises furthermore the steps b) and c)

b) chemically transforming compound of formula (I-A) to compound of formula (I-B)

c) chemically transforming compound of formula (I-B) or of formula (I-A) to compound of formula (I-C)

wherein step b) is optional.

In one variant (Var. I) the present process comprises the steps a) and b) and c). In other words, the reaction pathway is via the intermediate product of formula (I-B).

In the other variant (Var. II) the present process comprises the steps a) and c). In other words the reaction pathway is via the direct transformation of compound of formula (I-A) to compound of formula (I-C).

These two pathway are represented in the following reaction scheme.

The compound of formula (I-B) can be obtained for example by the reduction of formula (I-A), particularly by sodium boranate as disclosed by Kabbe and Heitzer, *Synthesis* 1978, 888-889.

The compound of formula (I-C) can be obtained from chemical transformation of compound of formula (I-B) by reduction, e.g. by partial hydrogenation, particularly by sodium/ethanol such as described in Schudel et al., *Helv. Chim. Acta*, 46, 2517-2526 (1963) the whole disclosure of which is incorporated herein by reference.

The compound of formula (I-C) can also be obtained from chemical transformation of compound of formula (I-A). This chemical transformation is particularly made by the reaction of metallic zinc in the presence of an acid or an acid mixture, for example as disclosed for in U.S. Pat. No. 6,096,907 the whole disclosure of which is incorporated herein by reference.

This direct transformation from compounds of formula (I-A) to (I-C) is advantageous because it is straight forward and avoids a multistage process.

The process of preparing tocotrienol quinone of formula (A) comprises furthermore the step f)

f) chemically transforming the R-isomer of compound of formula (I-C), represented by formula (II), to tocotrienol quinone of formula (A)

(II)

The tocotrienol quinone of formula (A) has the R-configuration. It can be obtained from compound of formula (II) particularly by oxidation with a suitable oxidant, particularly a metal salt with a high oxidation state, i.e. at least an oxidation state of (I+), particularly between (III+) and (VI+), such as for example a Fe(III) or Cer (IV) compound. Particularly suitable is the oxidation by ferric chloride (FeCl$_3$) preferably in an alcohol/water mixture, particularly methanol/water mixture, as disclosed in detail by *J. Org. Chem.* 1981, 46, 2445-2450 and CH 356754 for α-tocopherol the entire content of both is incorporated herein by reference. Further suitable are particularly mixtures of acetonitrile/water or acetonitrile/dichloromethane/water. The R-configuration is maintained.

Chromatographic Separation

The process of tocotrienol quinone of formula (A) further comprises steps d) and e)

d) chromatographic separation of the mixture of isomers of formula (I-A) or (I-B) or (I-C) by means of a chiral phase into the R-isomer (I) and residual (I');

e) collecting the R-isomer (I) being obtained by step d).

Chromatography is a known separation technique since a long time. It is basically also known that chiral compounds can be separated by means of using chiral phases.

For the present invention, the chiral phase is a chiral stationary phase (CSP). The chiral stationary phase can be prepared by attaching a suitable chiral compound to the surface of an achiral solid support such as silica gel. The chiral compound may be immobilized or form a coating on the support material. The chiral compound can be adsorbed or chemically bound to the support. Preferably the chiral compound is chemically bound to the support.

Such chiral phases are described in EP 0 157 365 A2, EP 0 155 637 A2, U.S. Pat. No. 7,772,153 B2, U.S. Pat. No. 4,619,970 and U.S. Pat. No. 4,861,872, the entire content of which is hereby incorporated by reference.

It is also possible in certain circumstances that the chiral compound can be used directly as such in the chiral separation. This is particular the case if the chiral compound is of mineral origin or if a highly molecular insoluble chiral polymer is used where no support material is needed.

Preferably, the chiral phase is a polysaccharide or a derivative thereof, particularly immobilized on an achiral solid support such as silica gel. Polysaccharides or derivatives thereof are described for example in *Pure Appl. Chem.*, Vol. 79, 2007, 1561-1573, the entire content of which is hereby incorporated by reference, as suitable chiral phases.

Particularly suitable chiral phases are those of the group consisting of celluloses, amyloses, chitins, chitosans, xylans, curdlans, dextrans, inulins and cyclodextrines and their derivatives.

Furthermore, in certain cases chiral phases selected from tartrate phases, polyacrylamide phases, chiral coordination complex phases or charge—transfer phases, chiral ion-exchange phases or Pirkle phases may be used for the purpose of the invention.

Particularly preferred chiral phases are those of the group consisting of celluloses, amyloses, dextrans and cyclodextrines and their derivatives.

Particularly suited are amylose tris(3,5-dimethylphenyl-carbamate), cellulose tris(3,5-dimethylphenylcarbamate), cellulose tris(3,5-dichlorophenyl-carbamate), cellulose tris (4-methylphenylcarbamate) or cellulose tris(4-methyl-benzoat) which are immobilized or coated on silica support.

Particularly suitable are the chiral phases which are commercially available under the trademarks Eurocel® (from Knauer GmbH, Germany), Regispack® (from Regis Technologies, Inc., USA) Chiralcel® and Chiralpak® (from Daicel Chemical Industries Ltd., Japan), preferably Chiralpak® IA, Chiralpak® IB, Chiralpak® IC and Chiralcel® OD, Chiralcel® OD-I from (from Daicel Chemical Industries Ltd., Japan).

The particle size of the chiral phase is in one embodiment smaller than 25 micrometer, particularly between 3 and 25 micrometer, preferably between 5 and 25 micrometer. Particularly preferred in this case, the chromatographic separation is undertaken by HPLC (High Performance Liquid Chromatography). It has been found that by using such small particle sizes a better separation of the isomers (in one chromatographic run) can be achieved, however, that a higher pressure is required. The pressure for this particle size is typically larger than 20 bar.

In another embodiment the particle size of the chiral phase is larger than 25 micrometer, particularly between 50 and 70 micrometer. It has been found that by using such larger particle sizes a lower pressure is required, but that the separation of the isomers (in one chromatographic run), however, is much lower. The pressure to be used for the chromatographic separation is for this particle size preferably between 1 and 18 bar, particularly between 2 and 17 bar, preferably between 5 and 15 bar.

It has been shown that an efficient separation can be preferably achieved if a hydrocarbon solvent is used as eluent. Particular suitable hydrocarbon solvents are aliphatic, cycloaliphatic or aromatic hydrocarbons such as $C_6$-$C_8$-alkane particularly n-octane, n-heptane, n-hexane as well as all the structural isomers thereof; cyclohexane, methylcyclohexane; benzene, ethylbenzene, xylene, and toluene or mixture thereof. Preferably only a single hydrocarbon, particularly hexane or heptane, is used as hydrocarbon solvent as eluent.

It has been found that it is preferential that the chromatographic separation in step d) is in presence of at least one alcohol.

As alcohol particularly suitable are alcohols selected from the group consisting of methanol, ethanol, 1-propanol, 2-propanol, 1-butanol, isobutanol, tert.-butanol, 2-methyl-2-butanol, 3-methyl-2-butanol, 3-methyl-1-butanol, 2-methyl-1-butanol and allylalcohol. Preferably the alcohol is n-propanol or isopropanol. Most preferred is 1-propanol.

Mixtures of alcohols may also be used.

It is preferred that the alcohol is part of the eluent, particularly present combined with the hydrocarbon solvent.

It has been further found that it is preferential that the chromatographic separation in step d) is in presence of at least an organic acid (S1) with a $pK_a$ of less than 6.0, particularly between 0.5 and 6.0, preferably between 3.0 and 6.0, being particularly acetic acid.

Examples for organic acids having with a $pK_a$ of between 3.0 and 6.0, are particularly citric acid, phthalic acid, terephthalic acid, succinic acid, cinnamic acid, formic acid, lactic acid, acetic acid, ascorbic acid, benzoic acid, butanoic acid, propanoic acid and octanoic acid.

Acids having a $pK_a$ of less than 6.0 are particularly those mentioned above as well as acids such as sulphonic acids or halogenated acids, particularly trifluoroacetic acid, trichloroacetic acid, p-toluenesulphonic acid, benzenesulfonic acid, dodecylbenzenesulfonic acid, methanesulphonic acid, trifluoromethane-sulfonic acid and nonafluorobutanesulphonic acid.

It has been shown that unexpectedly the presence of small amounts of an organic acid (S1) with a $pK_a$ of less than 6, particularly between 3.0 and 6.0, preferably acetic acid, enhances the loadability of the chiral phase. In other words by adding small amounts of organic acid larger quantities of isomers can be separated by a given chiral phase. This finding is very important in view of the cost calculation of equipment for an industrial separation.

It is preferred that the eluent used for the chromatographic separation in step d) comprises
- 85-100% by weight, particularly 90-98% by weight, of a hydrocarbon, particularly of a $C_6$-$C_8$-alkane;
- 0-10% by weight, particularly 0.1-5% by weight, of an alcohol, preferably 1-propanol;
- 0-5% by weight, particularly 0.1-2% by weight, of an organic acid (S1) with a $pK_a$ of less than 6.0, particularly between 3.0 and 6.0, preferably acetic acid.

Preferably the eluent comprises at least one a hydrocarbon, at least one alcohol and at least one organic acid with a $pK_a$ of less than 6.0, particularly between 3.0 and 6.0.

It has been found that for a particularly good separation Simulated Moving Bed (SMB) chromatography is used for the chiral chromatographic separation. Simulated Moving Bed (SMB) chromatography is a known method for separating racemic mixtures and is disclosed for example in U.S. Pat. No. 5,518,625 and WO 03/051867 A1, the entire contents of which is hereby incorporated by reference.

The steps d) and e) either take place after step a) or after step b) or after step c). It is preferred that steps d) and e) take place after step a) or after step b).

This means that the isomers are separated by separating the isomers of compound of formula (I-A) and/or of formula (I-B) and/or of formula (I-C).

Figure 1:
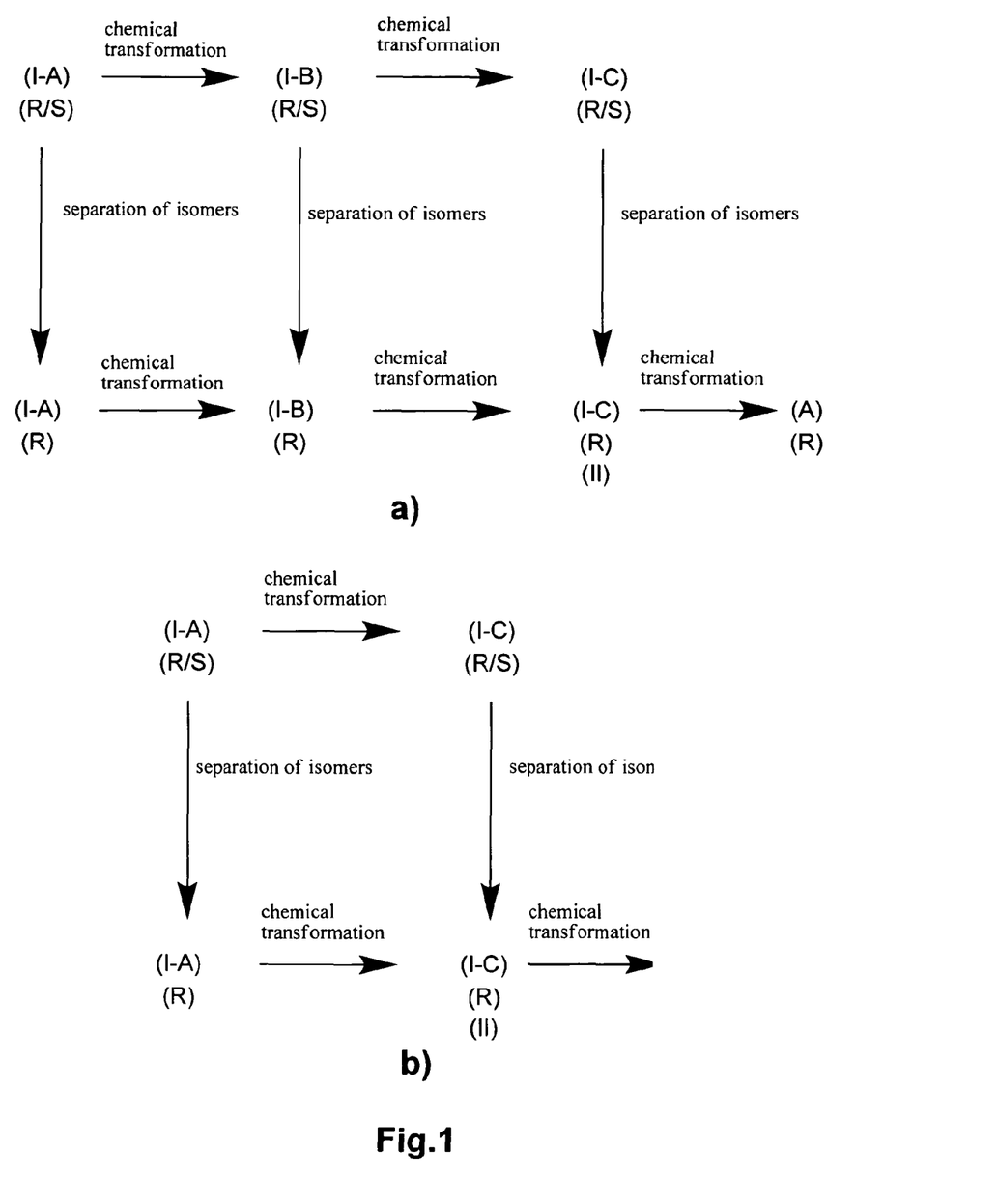

FIG. 1 a) shows schematically the different possibilities in the variant Var. I. The mixture of R- and S-isomers of formula (I-A) can be chemically transformed to R- and S-isomers of formula (I-B) (horizontal arrows). The mixture of R- and S-isomers of formula (I-A) can also be separated into the (desired) R-isomer of formula (I-A) (vertical arrow).

Analogously, the (desired) R-isomers of formula (I-B), respectively (I-C) may be obtained as it is represented in the scheme of FIG. 1a).

Furthermore, the R-isomer of formula (I-C)—being abbreviated as compound of formula (II)—is chemically transformed to tocotrienol quinone of formula (A) as described earlier in this document.

FIG. 1 b) shows schematically the different possibilities in the variant Var. II. The mixture of R- and S-isomers of formula (I-A) can be chemically transformed to R- and S-isomers of formula (I-C) (horizontal arrows). The mixture of R- and S-isomers of formula (I-A) can also be separated into the (desired) R-isomer of formula (I-A) (vertical arrow).

Analogously, the (desired) R-isomers of respectively (I-C) may be obtained as it is represented in the scheme of FIG. 1b).

Furthermore, the R-isomer of formula (I-C)—being abbreviated as compound of formula (II)—is chemically transformed to tocotrienol quinone of formula (A) as described earlier in this document.

The separation of the chiral isomers of formula (I-A) or (I-B) or (I-C) into the (desired) R-isomer (I) and the residual (I') by means of chiral phase can be complete or partial. The (desired) R-isomer (I) is the R-isomer of compound of formula (I-A) in case the separation takes place after step a). Accordingly the desired) R-isomer (I) is the R-isomer of compound of formula (I-B) in case the separation takes place after step b), respectively the desired) R-isomer (I) is the R-isomer of compound of formula (I-C) in case the separation takes place after step c).

In one embodiment the separation is essentially complete, preferable complete.

In order to explain the separation in more detail reference is made to FIGS. 2 to 8, which illustrate by means of schematic chromatograms, respectively diagrams, more details of these aspects of the invention. For simplicity's sake the peak having the lower retention time ($t_{ret}$) is assumed to have the R-configuration and the peak at the higher retention time ($t_{ret}$) has the S-configuration at the chiral centre indicated by *. Of course, in reality the sequence of R- and S-isomer strongly depends on the system and the column material and needs, therefore to be identified by further measurements or derivatisation methods.

Figure 2:
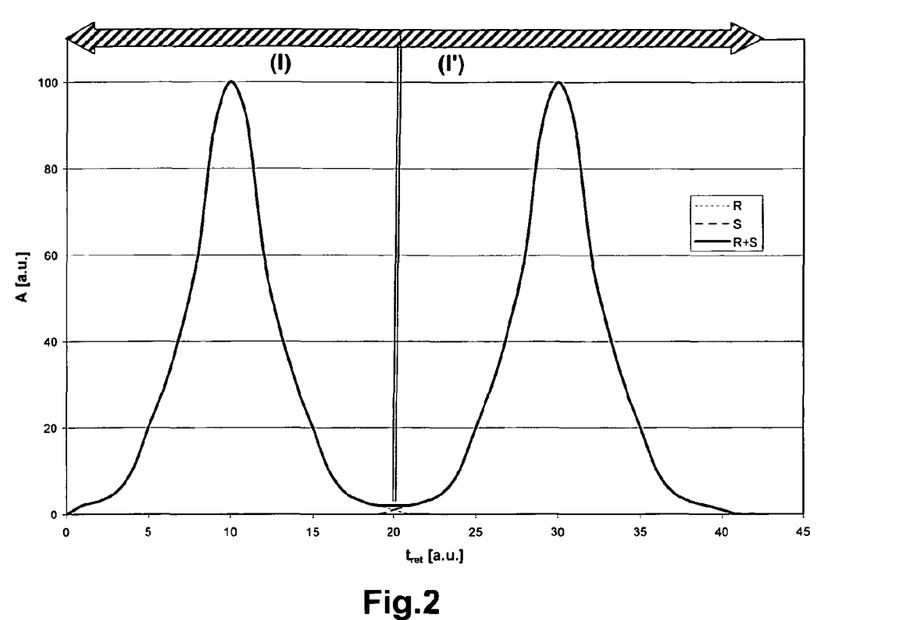
FIG. 2 shows in a schematic chromatogram the situation in which the chiral phase separates the (desired) R isomer (I) completely as the first eluted component.

FIG. 2 shows in a schematic chromatogram the situation in which the chiral phase separates the (desired) R isomer (I) completely as the first eluted component. The x-axis of the schematic chromatogram represents the retention time ($t_{ret}$) in arbitrary units (a.u.). The y-axis of the schematic chromatogram represents the absorbance (A) in arbitrary units (a.u.) by which the isomer distribution is detected. If the eluate (continuous line) is collected until a retention time indicated by the double line, the isomer R (dotted line) can be completely separated form the isomer S (dashed line).

Figure 3:
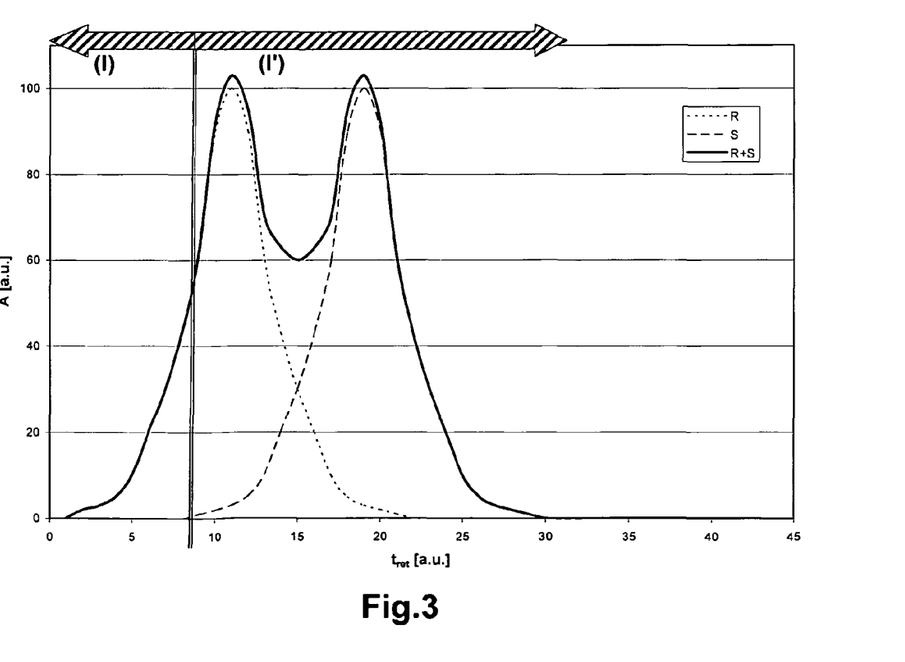
FIG. 3 shows, by means of an analogously schematic chromatogram to FIG. 2, the situation in which, the chiral phase separates the desired R-isomer (I) only partially.
Figure 4:
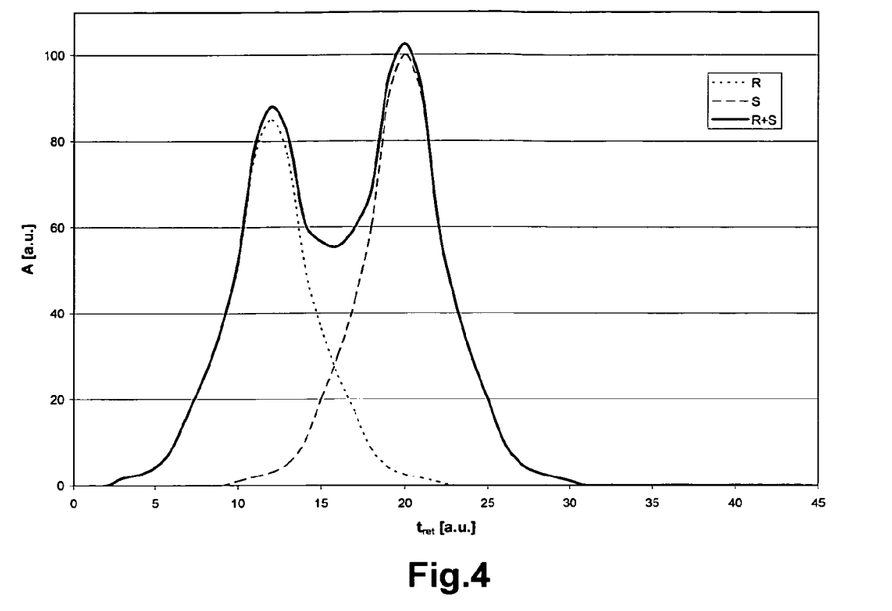
FIG. 4 is a schematic chromatogram showing residual isomers (I') and its respective R-isomer (dolled line) and S-isomer (dashed line)

FIG. 3 shows, by means of an analogously schematic chromatogram, the situation in which, however, the chiral phase separates the desired R-isomer (I) only partially. If the eluate (continuous line) is collected until a retention time indicated by the double line a part of the desired isomer R (dotted line) may be separated from the residual. The residual in this case comprises not only the isomer S (dashed line) but also some of the desired isomer R. In this schematic example only about 15% of the desired isomer is separated by the separation step b) and the residual (I'), hence, comprises 100% of the S-isomer and about 85% of the desired R-isomer. FIG. 4 shows this situation by a schematic chromatogram of the residual (I') and its isomers R (dotted line) resp. S (dashed line).

In a preferred embodiment of the invention the process of preparing tocotrienol quinone of formula (A) further comprises steps g) and h) which take place after step d)

g) isomerizing the chirality at the centre indicated by * in formula (I-A) or (I-B) or (I-C) of the isomers of the residual (I') being separated in step d);

h) adding the isomerized isomers obtained in step g) to a mixture of isomers being separated in step d) and which are object of further separation.

In one embodiment the isomerization in step g) takes place by exposure of the residual (I') to a temperature of above 150° C., particularly between 160 and 500° C. However the temperatures should not be too high to avoid undesired degradation of the isomers. Particularly suitable is a temperature of between 160 and 300° C. The isomerization can take place batchwise or continuously.

In another embodiment the isomerization in step g) takes place by exposure of the residual (I') to a base of which the corresponding acid has a $pK_a$ of larger than 13. The base has suitable basicity to deprotonate an keto-enol proton. Particularly suitable bases are alkoholates of alkali metals, particularly of sodium, potassium and lithium, particularly sodium methanolate and sodium ethanolate. The isomerization can take place batchwise or continuously.

It is preferred that the base being added is removed prior to step h). Preferably the removal is complete. The removal may particularly be undertaken by extraction or phase separation.

The base is preferable removed prior to step h), i.e. after the isomerization. This is advantageous in view of the isomerization stability of the final isomers.

In one embodiment the base of which the corresponding acid has a $pK_a$ of larger than 13 is immobilized on a solid carrier. In this embodiment the residual (I') being separated in step d) is preferably brought in contact, for example by passing through a column or a packed bed comprising the immobilized base.

The isomerization leads to a change of the configuration at the chiral centre indicated by * in formula (I-A) or (I-B) or (I-C). The isomerization in step g) leads to a change of the configuration at the centre indicated by *, so that, after isomerization, the ratio of numbers of molecules in the R-configuration to the one in the S-configuration is about 50:50. It is clear to the person skilled in the art that real isomerization may differ from a ratio of 50:50 despite the isomerization is complete. Although complete isomerization is desired, also incomplete isomerizations are useful for the present invention as long as the amount of desired isomer is increased by the isomerization. It has been found that the ratio of the amount of desired isomer:amount of the non-desired isomer is at least 25:75, particularly at least 30:70, preferably at least 40:60 after the isomerization step.

Figure 5:
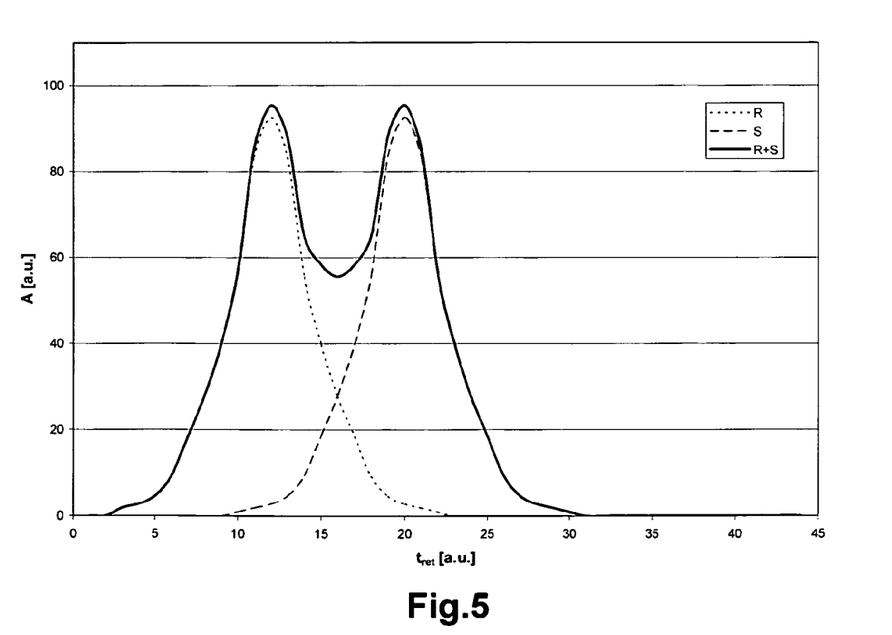
FIG. 5 is a schematic chromatogram showing an optimal situation of a ratio of 50:50.

The optimal situation of a ratio of 50:50 is shown by the schematic chromatogram of FIG. 5. As mentioned above for the example of separation of FIG. 3, resp. after separation of the desired isomer (I) for the residual (I') of FIG. 4, the isomerization leads in this example to a schematic chromatogram of FIG. 5 showing the isomerized residual (continuous line) and the individual isomers R (dotted line) respectively isomer S (dashed line).

In step h) the isomerized isomers which are obtained in step g) are added to a mixture of isomers being separated in step d) and which are object of further separation. Said mixture can be stored and transported or used at once.

Figure 6:
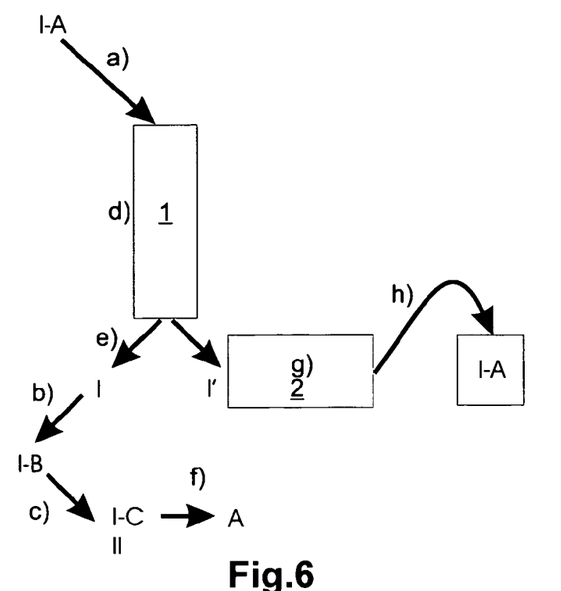
FIG. 6 shows a schematic representation for the embodiment in which the mixture is stored.

FIG. 6 shows a schematic representation for the embodiment in which said mixture is stored. In this representation exemplary a mixture of chiral isomers of formula (I-A) is provided in step a); chromatographically separated in step d) by means of a chiral phase 1 into R-isomer (I) and residual (I'); the isomers of the residual (I') are isomerized in step g) and then added to a mixture of isomers of formula (I-A)(step h). This mixture can be stored until a further separation is desired. In the shown representation the isomerization is performed by contacting the residual (I') with a column 2 comprising the immobilized base. The desired R-isomer (I) is collected in step e) and chemically transferred to compound (I-B) (step b) and subsequently to compound (I-C) (step c) and then transformed to tocotrienol quinine of formula (A) in step f).

It is, however, preferred that the process of the current invention is a continuous process, particularly in that the mixture of isomers of formula (I-A) or (I-B) or (I-C) being object of further separation is the mixture of isomers of formula (I-A) or (I-B) or (I-C) of step a), step b) or step c). So in other words, it is preferred that the isomerized isomers obtained in step g) are added to a stream of isomers of formula (I-A) or (I-B) or (I-C) in step a), step b) or step c).

Figure 7:
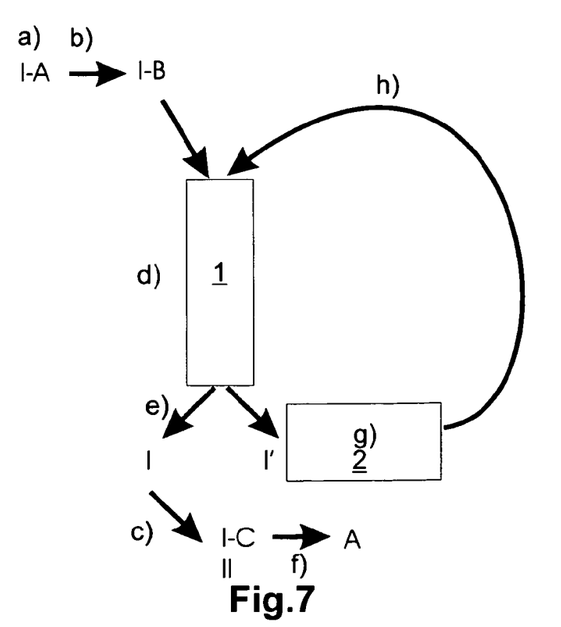
FIG. 7 shows a schematically representation of a chromatographic separation occurring after step b)

Such a situation is represented schematically in FIG. 7 for the chromatographic separation occurring after step b). In this representation exemplary a mixture of chiral isomers of formula (I-A) is provided in step a), chemically transformed to mixture of chiral isomers of formula (I-B) in step b), chromatographically separated in step d) by means of chiral phase 1 into desired isomer (I) and residual (I'); the isomers of the residual (I') isomerized in step g) and then fed to an incoming stream of mixture of isomers of an mixture of isomers of formula (I-B) in step h). In the shown representation the isomerization is performed by contacting the residual (I') with a column 2 comprising the immobilized base. The R-isomer collected in step e) is the R-isomer of compound (I-B) which is then chemically transformed in step c) to the R-isomer of compound of formula (I-C), also abbreviated as compound of formula (II) which then is chemically transformed to the compound of formula (A) in step f).

This process is much preferred as it allows in a very cost efficient way to produce continuously the desired isomer (I) collected in step e), i.e. directly after the separation of desired isomer (I) and residual (I') in step b).

The process of separating chiral isomers of formula (I-A) or (I-B) or (I-C) comprises a further step e) collecting the R-isomer (I) being obtained by step d)

Said R-isomer (I) is preferably collected directly after chromatographic separation in step d).

Said process produces in an efficient way the R-isomer (I) out of a mixture of at least two isomers of formula (I-A) or (I-B) or (I-C). The process is the more efficient the better the separation of the isomers is in step d).

It has been observed that said separating efficiency is higher if particle sizes of the chiral phase is in one embodiment smaller than 25 micrometer, particularly between 3 and 25 micrometer are used in combination with HPLC, particularly in case that the eluent used for the chromatographic separation in step b) comprises a hydrocarbon and an alcohol and/or an organic acid (S1) with a $pK_a$ of less than 6.0, particularly between 3.0 and 6.0.

However, when high pressure in the chromatography particularly when Simulated Moving Bed (SMB) chromatography is used, there arise high requirements for the equipment allowing a reliable continuous production. Particularly high technical requirements are those for the pumps, valves and joints. These high requirements lead to a remarkable costly expenditure.

As the condition of the present process are leading neither to deterioration nor to remarkable degradation of the compounds of formula (I-A) or (I-B) or (I-C) the number of cycles d)-g)-h) is not very critical, in case when steps g) and h) are used. Hence, a lower efficiency in separating the isomers of the isomers (I-A) or (I-B) or (I-C) due to larger particle sizes of the chiral phase, i.e. larger than 25 micrometer, combined with lower pressure is not necessary disadvantageous per se as lower expenditure is necessary in view of equipment and maintenance. Therefore, it may be financially well favourable to operate the separation process on a manifold of low-cost columns or SMB-units operated at low pressure and using several additional cycles rather than using high pressure SMB equipment with columns packed with particles between 3 and 25 micrometer having high separation efficiency.

Figure 8:
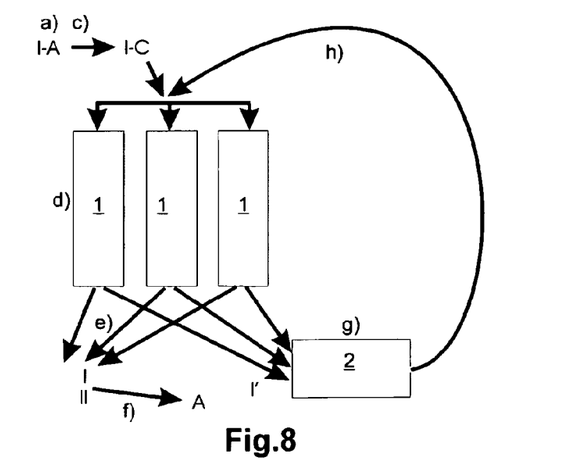
FIG. 8 shows a schematic representation of a process using multiple separation columns or multiple SMB-units 1.

FIG. 8 shows a schematic representation of a process using multiple separation columns or multiple SMB-units 1. In this representation the mixture of compounds of formula (I-A) are chemically transformed to compounds of formula (I-C) the mixture of isomers of formula (I-C) in step c) in a direct way, i.e. not via the compound of formula (I-B). This mixture of isomers of compounds of formula (I-C) is separated by columns or multiple SMB-units 1 used in parallel arrangement to yield each of them the R-isomer (I), as desired isomer, which is collected and the residual (I'). The residual (I') then is isomerized and re-fed into the stream of isomers of formula (I-C). The column, resp. SMB-unit 1, shown in separation process is operated at low pressure of typically between 5 and 15 bar and uses chiral phase of particle size of more than 25 micrometer. The separation efficiency is relative low which can be visualized by the schematic chromatogram represented by FIG. 3. In the shown representation the isomerization is performed by contacting the residual (I') with a column 2 comprising the immobilized base.

The disclosed process enables separating the isomers in industrial scale. In using the process, particularly the steps d), g), h) and e), in a continuous way almost all undesired isomers can be converted to the desired isomer due to the isomerization step. Hence, almost no undesired isomers being produced by non stereospecific synthesis need to be discarded and, hence, a yield of essentially 100% in the desired isomer, i.e. the R-isomer, can be obtained. This is economically and ecologically particular advantageous and, therefore, represents a remarkable and important step forward in the development in this field of technology.

The process as described before in detail leads to tocotrienol quinone of formula (A) in a very specific and efficient way. The tocotrienol quinone of formula (A) is obtained by the above process in a very high enantiomeric purity, i.e. the weight ratio of S-enantiomer to the R-enantiomer (formula A) is preferably less than 1/99, more preferably less than 0.1/99.9.

The tocotrienol quinone of formula (A) can be further chemically transformed to tocotrienol hydroquinone of formula (B).

(B)

The transformation from tocotrienol quinone of formula (A) to tocotrienol hydroquinone of formula (B) can be achieved by chemical reduction. This reduction takes preferably place by treating the tocotrienol quinone of formula (A) with a suitable reduction agent.

Suitable reduction agents are particularly hydrosulfites (dithionites), such as potassium dithionite or sodium dithionite; hydrides, such as sodium borohydride or potassium borohydride. Furthermore particularly suitable is the reduction with sodium dithionite as described in detail in example 2 of CH 356754 for the corresponding hydroquinone of α-tocopherol the entire content of both is incorporated herein by reference.

Hence, a further aspect of the present invention is a process of preparing tocotrienol hydroquinone of formula (B) which is obtained by chemical reduction from tocotrienol quinone of formula (A) which has been prepared as previously described in this document in detail.

Tocotrienol quinone of formula (A) and tocotrienol hydroquinone of formula (B) can be used in several fields of application. Particularly, they find use in the field of food or feed or beverage or pharmaceuticals. Particularly in these fields it is very advantageous or is even necessary to offer chiral compounds in a predetermined chirality. Particularly beneficial for these fields of application is if only a single desired isomer, preferably the R-isomer, out of an initial isomer mixture can be separated. The present process is enabling that target.

Therefore, a further aspect of the present invention is a food or feed or beverage comprising at least a compound of formula (A) or (B) which has been prepared by a process as described before in detail in this document.

These food or feed or beverages can have beneficial effect to the animal, respectively the human, consuming food or feed or beverages. Said food or feed or beverages may comprise further ingredients which are known to the person skilled in this technical field as well as the method of preparing such a food or feed or beverage.

A further aspect of the present invention is a pharmaceutical composition comprising at least a compound of formula (A) or (B) which has been prepared by a process as described before in detail in this document.

Such a pharmaceutical composition typically comprises further ingredients, particularly a non-toxic carrier. Suitable further ingredients of such a pharmaceutical composition are known to the person skilled in the art as well as the galenic formulation and preparation allowing the ingredients to action in a desired way. The pharmaceutical composition can be administered preferably orally, anally, topically or by inhalation or by injection. Most preferred the pharmaceutical composition is administered orally, particular in form of a capsule or a tablet.

The pharmaceutical composition is particularly used for the treatment of Leight Syndrome, of ophthalmic diseases or mitochondrial diseases, of oxidative stress and ageing of the body as well as for the treatment of high cholesterol level in blood.

LIST OF REFERENCE SIGNS

1 Chiral phase, column, SMB-unit
2 Column comprising the immobilized base
I desired isomer
I' residual
I-A mixture of chiral isomers of formula (I-A)

EXAMPLES

The present invention is further illustrated by the following experiments.
1. Chromatographic Separation
Starting Materials:
Solvents and reagents used as received were heptane (Fluka, 51750), ethanol (Merck, 1.00983), isopropanol (Sigma-Aldrich, 59300) and acetic acid (Fluka, 45730).
Chromatography:
Preparative separations were performed on an Agilent 1100 series hplc system consisting of an Agilent 1100 degasser, Agilent 1100 preparative pump, Agilent 1100 diode array detector, Agilent 1100 MPS G2250A autosampler/fraction collector controlled by chemstation/CC-mode software package.
HPLC Conditions for Preparative Separation:
Column: Daicel Chiracel® OD-H, 250 mm×20 mm; eluent 0.5% isopropanol, 0.2% acetic acid in n-heptane; flow 13 ml/min; detection 220 nm, 400 µl injection.

Separation of (R)-6-hydroxy-2,5,7,8-tetramethyl-2-((3E,7E)-4,8,12-trimethyltrideca-3,7,11-trienyl)chroman-4-one and (S)-6-hydroxy-2,5,7,8-tetramethyl-2-((3E,7E)-4,8,12-trimethyltrideca-3,7,11-trienyl)chroman-4-one Example 1

6-Hydroxy-2,5,7,8-tetramethyl-2-((3E,7E)-4,8,12-trimethyltrideca-3,7,11-trienyl) chroman-4-one was prepared according to the example 6a in Kabbe and Heitzer, *Synthesis* 1978, 888-889.

Figure 9:
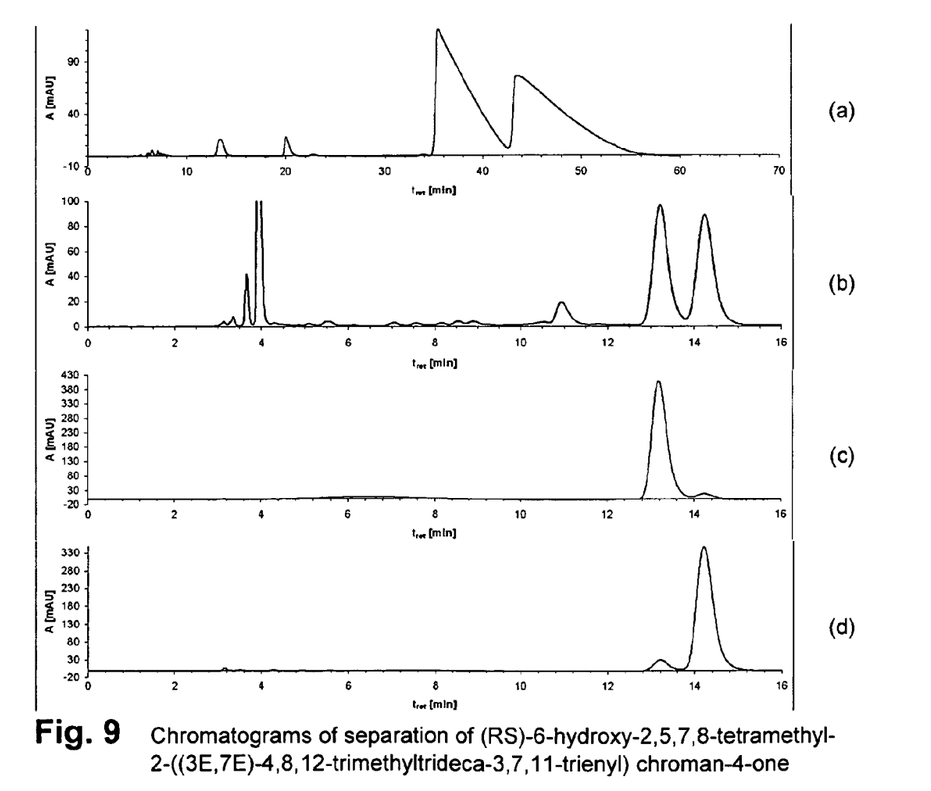
FIG. 9 show chromatograms of the separation of (RS)-6-hydroxy-2,5,7,8-tetramethyl-2-((3E,7E)-4,8,12-trimethyl-trideca-3,7,11-trienyl) chroman-4-one.

The product was analyzed by HPLC (Column: Daicel Chiracel® OD-H, 250 mm×4.6 mm; eluent 1% ethanol in n-hexane; flow 1 ml/min; detection 220 nm, 2 µl injection). FIG. 9 b) shows this chromatogram. It shows that the product is a 49.5:50.5 mixture (Retention time 13.2 and 14.2 min.)

87.5 mg of this product in heptane was injected and the two peaks with retention time at maximum 35.4 min. (1) (50.9%) resp. 43.5 min. (2) (49.1%) were separated by the preparative HPLC separation. FIG. 9 a) shows the chromatogram of the preparative HPLC separation.

After evaporation to dryness and dissolution the two collected fractions have been reanalysis on an analytical column (Daicel Chiracel® OD-H, 250 mm×4.6 mm; eluent 1% ethanol in n-hexane; flow 1 ml/min; detection 220 nm, 2 µl injection). FIG. 9 c), respectively FIG. 9 d), show the chromatogram of the first fraction, respectively the second fraction. The separation of the two isomers (Retention time 13.2 min, resp. 14.2 min) in the two fraction shows to be 94.9:5.1 (FIG. 9 c)) resp. 7.1:92.9 (FIG. 9 d)). Hence, the two isomers have been separation by preparative chromatography almost completely.

The invention claimed is:
1. A process of preparing tocotrienol quinone of formula (A):

(A)

the process comprising the steps
a) providing an isomeric mixture of compounds of formula (I-A)

(I-A)

b) chemically transforming compound of formula (I-A) to compound of formula (I-B)

(I-B)

c) chemically transforming compound of formula (I-B) or of formula (I-A) to compound of formula (I-C)

(I-C)

d) chromatographically separating the mixture of isomers of formula (I-A) or (I-B) or (I-C) by means of a chiral phase into the R-isomer (I) and residual (I');

e) collecting the R-isomer (I) being obtained by step d);
f) chemically transforming the R-isomer of compound of formula (I-C), represented by a compound of formula (II) by oxidation of the compound of formula (II) by a metal in an oxidation state of at least (I+) to tocotrienol quinone of formula (A)

wherein
$R^1$, $R^3$ and $R^4$ are independently from each other hydrogen or methyl groups;
$R^2$ represents hydrogen or a phenol protection group;
$R^5$ represents a residue of formula (II-B):

wherein * represents the chiral centre of the chiral isomer of formula (I-A) or (I-B) or (I-C); and
wherein step b) is optional and steps d) and e) take place either after step a) or after step b) or after step c).

2. The process according to claim 1, wherein the process further comprises after step d) the following steps g) and h):
g) isomerizing the chirality at the centre indicated by * in formula (I-A) or (I-B) or (I-C) of the isomers of the residual (I') being separated in step d); and
h) adding the isomerized isomers obtained in step g) to a mixture of isomers being separated in step d) and which are object of further separation.

3. The process according to claim 2, wherein the isomerization in step g) takes place by exposing the residual (I') to a temperature of above 150° C.

4. The process according to claim 2, wherein the isomerization in step g) takes place by exposing the residual (I') to a base of which a corresponding acid has a p$K_a$ of larger than 13.

5. The process according to claim 1, wherein the chemical transformation in step f) is practiced by oxidation of the compound of formula (II) by Fe(III) or Ce(IV).

6. The process according to claim 1, wherein or or or

7. The process according to claim 1, wherein $R^2$ is H.

8. The process according to claim 1, wherein $R^2$ is a phenol protection group, and wherein step i) comprises removing the protection group, and wherein step i) takes place before or after or during any one of the steps b) to g) or before or during step f).

9. The process according to claim 1, wherein the chiral phase is a chiral phase of the group consisting of celluloses, amyloses, dextrans and cyclodextrines and derivatives thereof.

10. The process according to claim 1, wherein the chiral chromatographic separation uses a Simulated Moving Bed (SMB) chromatography.

11. The process according to claim 1, wherein the chromatographic separation in step d) is practiced in the presence of at least one alcohol.

12. The process according to claim 1, wherein the chromatographic separation in step d) is practiced in the presence of at least an organic acid (S1) with a p$K_a$ of less than 6.0.

13. A process of preparing tocotrienol hydroquinone of formula (B):

wherein the process comprises obtaining the tocotrienol hydroquinone by chemical reduction from tocotrienol quinone of formula (A) prepared according to claim 1.

14. The process according to claim 11, wherein the alcohol is at least one selected from the group consisting of methanol, ethanol, 1-propanol, 2-propanol, 1-butanol, isobutanol, tert.-butanol, 2-methyl-2-butanol, 3-methyl-2-butanol, 3-methyl-1-butanol, 2-methyl-1-butanol and allylalcohol.

15. The process according to claim 12, wherein the p$K_a$ of the organic acid (S1) is between 3.0 and 6.0.

16. The process according to claim 15, wherein the organic acid (S1) is acetic acid.

17. The process according to claim 3, wherein the residual (I') is exposed to a temperature between 160 and 500° C.

18. The process according to claim 3, wherein the residual (I') is exposed to a temperature between 160 and 300° C.

* * * * *